United States Patent
Salma et al.

(10) Patent No.: US 7,438,877 B2
(45) Date of Patent: Oct. 21, 2008

(54) FAST, HIGH CAPACITY HYDROGEN SULFIDE SCAVENGERS

(75) Inventors: Tauseef Salma, Sugar Land, TX (US); Alexander A. Lambert, III, Houston, TX (US); Gordon T. Rivers, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 47 days.

(21) Appl. No.: 11/514,594

(22) Filed: Sep. 1, 2006

(65) Prior Publication Data

US 2008/0056974 A1 Mar. 6, 2008

(51) Int. Cl.
C02F 1/68 (2006.01)
C10G 29/20 (2006.01)

(52) U.S. Cl. .................. 423/220; 423/242.7; 48/127.3; 48/127.5; 208/14; 208/208 R; 208/236; 210/749; 210/750; 210/916

(58) Field of Classification Search ................ 48/127.3, 48/127.5; 208/14, 208 R, 236; 210/749, 210/750, 916; 252/189, 190; 423/220, 242.7; 544/1, 180
See application file for complete search history.

(56) References Cited

U.S. PATENT DOCUMENTS

| 2,496,596 | A | 2/1950 | Moyer et al. |
| 2,596,273 | A | 5/1952 | Moyer et al. |
| 2,596,425 | A | 5/1952 | Moyer et al. |
| 2,729,679 | A | 1/1956 | Anderson |
| 3,791,974 | A | 2/1974 | Borchert |
| 4,978,512 | A | 12/1990 | Dillon |
| 5,128,049 | A | 7/1992 | Gatlin |
| 5,314,672 | A | 5/1994 | Vasil |
| 5,347,004 | A | 9/1994 | Rivers et al. |
| 5,488,103 | A | 1/1996 | Gatlin |
| 5,554,349 | A | 9/1996 | Rivers et al. |
| 5,674,377 | A * | 10/1997 | Sullivan et al. ......... 208/208 R |
| 5,698,171 | A | 12/1997 | Trauffer et al. |
| 5,744,024 | A | 4/1998 | Sullivan, III et al. |
| 5,958,352 | A | 9/1999 | Callaway et al. |
| 6,582,624 | B2 | 6/2003 | Titley et al. |
| 6,663,841 | B2 * | 12/2003 | Salma et al. ............. 423/437.1 |
| 2005/0238556 | A1 * | 10/2005 | Pakulski et al. ............. 423/228 |

FOREIGN PATENT DOCUMENTS

| GB | 920301 | 3/1963 |
| GB | 2290542 A * | 1/1996 |

OTHER PUBLICATIONS

Jan M. Bakke et al. "Hydrogen Sulfide Scavenging by 1,3,5-Triazinanes. Comparison of the Rates of Reaction." Ind. Eng. Chem. Res., vol. 43, No. 9 (2004), pp. 1962-1965.*
J. F. Walker, Formaldehyde, 1964, pp. 360-361, 610, 613, Reinhold, New York.

* cited by examiner

*Primary Examiner*—Timothy C Vanoy
(74) *Attorney, Agent, or Firm*—Madan Mossman & Sriram PC

(57) ABSTRACT

Selective, irreversible removal of hydrogen sulfide ($H_2S$) and other sulfhydryl compounds from a gas stream, such as sour natural gas and sour hydrocarbon liquids is achieved with a scavenging agent having hydroxyalkyl functionality and alkylamine functionality. This scavenger possesses a higher capacity for $H_2S$ removal compared with a scavenger having only hydroxyalkyl functionality. The scavenging agent is made by reacting at least one alkanolamine and at least one alkyl amine with an aldehyde, such as formaldehyde.

24 Claims, 1 Drawing Sheet

FAST, HIGH CAPACITY HYDROGEN SULFIDE SCAVENGERS

TECHNICAL FIELD

The invention relates to chemical compositions and methods for scavenging sulfhydryl compounds, particularly hydrogen sulfide ($H_2S$), from "sour" aqueous and hydrocarbon substrates, and more particularly relates, in one non-limiting embodiment, to methods and compositions useful as scavengers to remove sulfhydryl compounds from natural gas.

BACKGROUND

The removal of $H_2S$ and other sulfhydryl compounds from a liquid or gaseous hydrocarbon stream is a problem that has challenged many workers in many industries. One such industry is the petroleum industry, where the $H_2S$ content of certain crudes from reservoirs in many areas of the world is too high for commercial acceptance. The same is true of many natural gas streams. Even where a crude or gas stream contains only a minor amount of sulfur, the processes to which the crude oil or fractions thereof are subjected often produce one or more hydrocarbon streams that contains $H_2S$.

The presence of $H_2S$ in hydrocarbon streams presents many environmental and safety concerns. Hydrogen sulfide is highly flammable, toxic when inhaled, and strongly irritates the eyes and other mucous membranes. In addition, sulfur-containing salts can deposit in and plug or corrode transmission pipes, valves, regulators, and the like. Flaring of natural gas that contains $H_2S$ does not solve the problem for gas streams because, unless the $H_2S$ is removed prior to flaring, the combustion products will contain unacceptable amounts of pollutants, such as sulfur dioxide ($SO_2$)—a component of "acid rain."

Hydrogen sulfide has an offensive odor, and natural gas containing $H_2S$ often is called "sour" gas. Treatments to reduce or remove $H_2S$ from hydrocarbon or other substrates often are called "sweetening" treatments. The agent that is used to remove or reduce $H_2S$ levels sometimes is called a "scavenging agent" or "scavenger". The sweetening or scavenging of $H_2S$ from petroleum or natural gas is only one example of where $H_2S$ level reduction or removal must be performed. Many aqueous substrates also must be treated to reduce or remove $H_2S$.

In the manufactured gas industry, or the coke-making industry, the destructive distillation of bituminous coal with a high sulfur content commonly produces coal gas containing an unacceptable amount of $H_2S$. Another $H_2S$ contamination problem arises during the manufacture of water gas or synthesis gas. Water gas or synthesis gas streams that contain $H_2S$ often are produced by passing steam over a bed of incandescent coke or coal. The incandescent coke or coal often contains a minor amount of sulfur, which contaminates the resulting gas stream.

The problem of removing or reducing $H_2S$ from hydrocarbon and aqueous substrates has been solved in many different ways in the past. Most of the known techniques involve either (a) absorption, or selective absorption by a suitable absorbent, after which the absorbent is separated and the sulfur removed to regenerate and recycle the absorbent, or (b) selective reaction with a reagent that produces a readily soluble product. A number of known systems treat a hydrocarbon stream with an amine, an aldehyde, an alcohol, and/or a reaction product thereof. The wide variety of processes, patents, and publications that describe methods for removing $H_2S$ from hydrocarbon streams is evidence that it is desirable and necessary to remove $H_2S$ from aqueous and hydrocarbon streams.

A continuing need exists for alternative processes and compositions to reduce and/or remove $H_2S$ from aqueous and hydrocarbon substrates. The need for removing sulfhydryl compounds from hydrocarbon substrates has increased as the world's supply of "sweet" natural gas and crude oil is reduced. It would thus be desirable to discover and/or develop new scavenging agents that are fast and have a high capacity for removing sulfhydryl compounds as compared with known scavengers.

SUMMARY

There is provided, in one form, a method for reducing the amount of sulfhydryl compounds in sour aqueous and sour hydrocarbon substrates that involves scavenging the sulfhydryl compounds from the substrate with a scavenging agent that contains a triazine which has both hydroxyalkyl and alkylamine functionality. The scavenging agent is present in an amount sufficient to reduce said amount of said sulfhydryl compounds in said substrate.

There is further provided in another non-limiting embodiment a method for reducing an amount of sulfhydryl compounds in sour hydrocarbon gas that concerns scavenging the sulfhydryl compounds from the gas with a triazine scavenging agent. The agent is present in an amount ranging from about 0.00045 to about 13.4 gallons per ppm of sulfhydryl compound to be removed×MMscf of gas (0.06 to 1790 liters scavenger used/(ppm sulfhydryl compound removed× MMscm)), where the triazine has the structure:

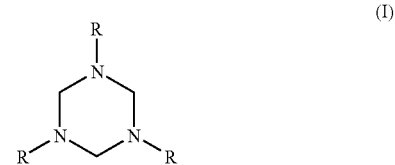

(I)

In structure (I) the R groups are independently selected from the group consisting of $C_1$-$C_{20}$ straight or branched alkyl groups, or —$R_1$OH, where $R_1$ is a $C_1$-$C_{20}$ straight or branched alkylene group. At least one R group is $C_1$-$C_{20}$ straight or branched alkyl groups and at least one R group is —$R_1$OH.

There is additionally provided in another non-restrictive version a substrate treated for at least one sulfhydryl compound. The treated substrate may be a sour aqueous substrate, a sour hydrocarbon substrate or a mixture thereof. The substrate further contains at least one sulfhydryl compound and a scavenging agent that includes a triazine which has both hydroxyalkyl and alkylamine functionality. The scavenging agent is present in an amount sufficient to reduce the amount of the sulfhydryl compounds in the substrate as compared with the same substrate absent the scavenging agent.

Further there is provided a sour hydrocarbon gas that is treated for at least one sulfhydryl compound, where the gas includes a triazine scavenging agent in an amount of from about 0.00045 to about 13.4 gallons per ppm of sulfhydryl compound to be removed×MMscf of gas (about 0.06 to about 1790 liters scavenger used/(ppm sulfhydryl compound removed×MMscm)). The triazine has the structure (I) above.

DETAILED DESCRIPTION

Figure 1:
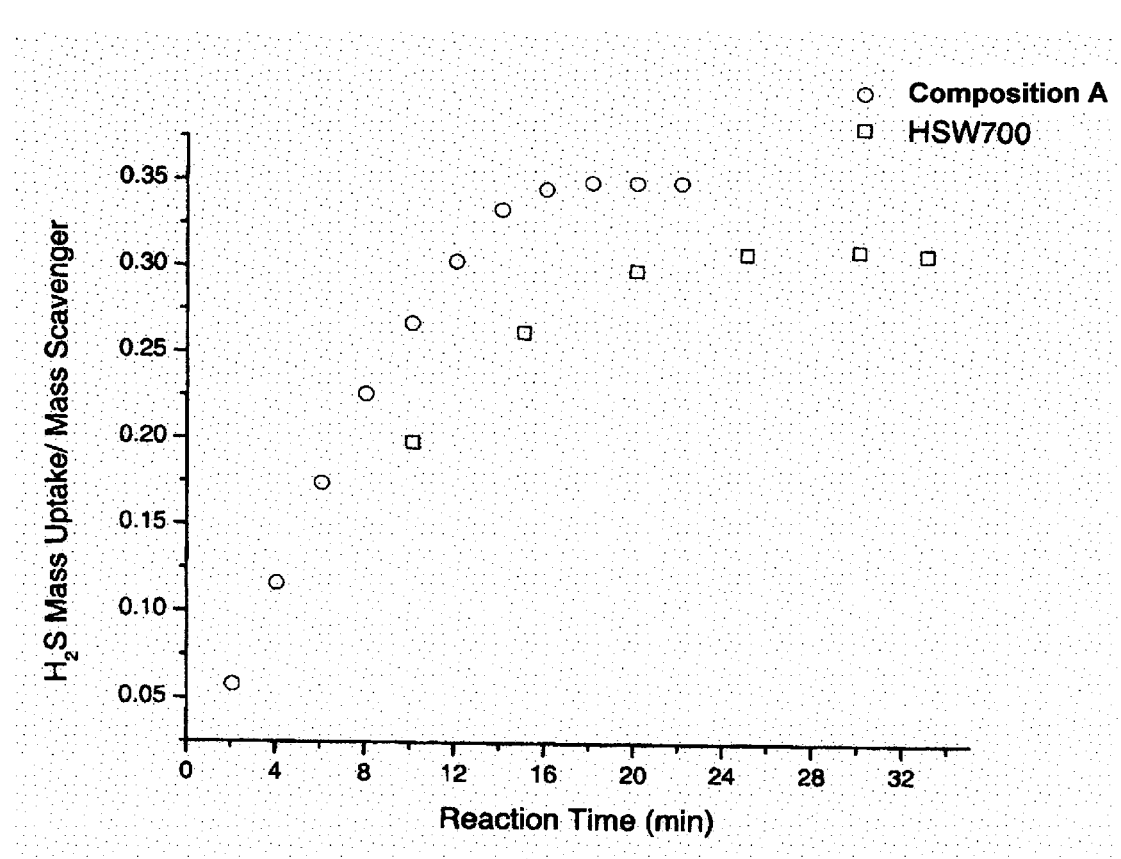
FIG. 1 is a graph of the ratio of $H_2S$ mass uptake to the mass of scavenger as a function of time for a triazine of the invention (Composition A) compared to a comparative, monoethanolamine triazine (HSW700) having no alkylamine functionality.

It has been discovered that triazine compounds having at least one hydroxyl functionality, such as a hydroxyalkyl, and at least one alkylamine functionality permit selective removal of sulfhydryl compounds, particularly $H_2S$, from a gas or liquid containing the same rapidly and with high capacity. By "selectively" is meant that the sulfhydryl compound is removed relatively faster and in greater proportion compared to another compound present in the gas or liquid, particularly carbon dioxide ($CO_2$). These compounds are expected to irreversibly remove $H_2S$ from sour liquid or gas hydrocarbon streams.

The scavenging agents of the present methods and compositions may be used to treat aqueous and hydrocarbon substrates that are rendered "sour" by the presence of sulfhydryl compounds, such as hydrogen sulfide ($H_2S$), organosulfur compounds having a sulfhydryl (—SH) group, known as mercaptans, also known as thiols (R—SH, where R is a hydrocarbon group), thiol carboxylic acids (RCO—SH), dithio acids (RCS—SH), and related compounds.

As used herein, the term "aqueous substrate" refers to any "sour" aqueous substrate, including waste water streams in transit to or from municipal waste water treatment facilities, tanning facilities, and the like.

The term "hydrocarbon substrate" is meant to include unrefined and refined hydrocarbon products, including natural gas, derived from petroleum or from the liquefaction of coal, both of which contain hydrogen sulfide or other sulfur-containing compounds. Thus, particularly for petroleum-based fuels, the term "hydrocarbon substrate" includes, but is not limited to, wellhead condensate as well as crude oil which may be contained in storage facilities at the producing field. "Hydrocarbon substrate" also includes the same materials transported from those facilities by barges, pipelines, tankers, or trucks to refinery storage tanks, or, alternately, transported directly from the producing facilities through pipelines to the refinery storage tanks. The term "hydrocarbon substrate" also includes refined products, interim and final, produced in a refinery, including distillates such as gasolines, distillate fuels, oils, and residual fuels. As used in the claims, the term "hydrocarbon substrate" also refers to vapors produced by the foregoing materials.

A wide variety of aqueous and hydrocarbon substrates can be treated using the scavenging agents herein, one particularly suitable substrate being natural gas. The triazines may in one non-limiting embodiment be added to the substrate at a high enough temperature that the substrate is flowable for ease in mixing. The treatment may take place at temperatures up to the temperature at which the material being treated begins to decompose. In another non-restrictive version, treatment temperatures may be between ambient to about 66° C. (150° F.).

In one non-restrictive embodiment, the active triazine in the scavenging agent has the structure:

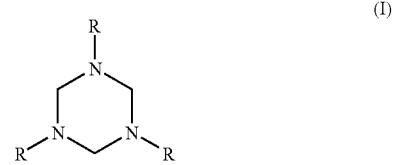

where the R groups are independently selected from the group consisting of $C_1$-$C_{20}$ straight or branched alkyl groups, or —$R_1OH$, where $R_1$ is a $C_1$-$C_{20}$ straight or branched alkylene group, where at least one R group is $C_1$-$C_{20}$ straight or branched alkyl groups and at least one R group is —$R_1OH$.

In one particularly useful embodiment, at least one of the R groups is —$R_1OH$ where $R_1$ is $C_2$ alkylene (hydroxyethylene), and where at least one R group is methyl.

The triazine scavengers herein are formed by reacting alkanolamines and alkyl amines with an aldehyde compound to form the multifunctional amine products. In one non-limiting embodiment, the aldehyde may be formaldehyde. In another non-restrictive embodiment, the primary alkyl amine reactant contains 1 to 20 carbon atoms and the alkanolamine reactant contains 1 to 20 carbon atoms. More specifically, suitable alkyl amines include, but are not necessarily limited to, methylamine, ethylamine, propylamine, isopropylamine, butylamine, iso-butylamine and mixtures thereof. Further, suitable alkanolamines include, but are not necessarily limited to, ethanolamine (2-aminoethanol), iso-propanolamine 1-amino-2-propanol), aminopropanol (3-amino-1-propanot), aminomethylpropanol (2-amino-2-methylpropanol), trishydroxymethylmethylamine (2-amino-2-hydroxymethyl-1,3-propanediol) and mixtures thereof.

In one non-limiting embodiment, the scavenging agent is formed by reacting formaldehyde with at least one primary amine and at least one alkanolamine, where the molar ratio of formaldehyde to total amines ranges from about 2:1 to about 1:2. Alternatively, non-restrictive molar ratios of formaldehyde to total amines range from about 1.5:1 up to about 1:1.5, and in another non-limiting embodiment from about 1.15:1 to 1:1.15. The molar ratio of alkyl amine to alkanolamine may range from about 99:1 to about 1:99; alternatively from about 90:10 to about 10:90, and in a different, non-restrictive embodiment from about 75:25 to about 25:75. Generally, the reaction is an exothermic one, thus the evolved heat should be controlled such as by removing heat, adding the components at a controlled, slow rate, and the like.

The triazines of formula (I) exhibit a high uptake capacity for hydrogen sulfide, and the raw materials required to manufacture the triazines are relatively low cost materials.

It is not always easy in advance to determine the effective proportion of triazine scavenger for a particular substrate due to the variance in makeup and type of substrate, the particular triazine employed and the physical conditions that the scavenging operation takes place. In the non-limiting condition where the substrate is a gas, the amount of scavenging agent may range from about 0.00045 to about 13.4 gallons per ppm of sulfhydryl compound to be removed×MMscf of gas (about 0.06 to about 1790 liters scavenger used/(ppm sulfhydryl compound removed×MMscm)). Alternatively, the lower end of this range may be about 0.0045 or even about 0.045 gallons per ppm of sulfhydryl compound to be removed×MMscf of gas (about 0.6 or about 6.0 liters scavenger used/(ppm sulfhydryl compound removed×MMscm)), whereas the upper end of the range may independently be about 1.34 or even about 0.134 gallons per ppm of sulfhydryl compound to be removed×MMscf of gas (about 179 or even about 17.0 liters scavenger used/(ppm sulfhydryl compound removed× MMscm)).

The invention will be further described with respect to the following Examples which are not meant to limit the invention, but rather to further illustrate the various embodiments.

EXAMPLES

Example 1

Preparation of Dual Hydroxyl/Alkylamine Functionality Triazine

Formaldehyde, monomethylamine (MMA) and monoethanolamine (MEA) were reacted together in the proportions shown in Table I.

TABLE I

| Example 1 Components by Weight Percent | |
|---|---|
| Formaldehyde (50)* | 41.404 |
| MMA (50)* | 25.410 |
| MEA | 19.206 |
| Glacial Acetic Acid | 1.171 |
| Methanol | 8.451 |
| Bellasol S30 | 1.600 |
| Water | 2.759 |

*50% by weight, balance is water

The acetic acid, methanol and water are solvents. Bellasol S30 is a scale inhibitor available from OSP Microcheck, Inc.

Production Protocol

1. Charge reactor with formaldehyde. Agitate vessel.
2. Add MMA at a controlled rate. This is an exothermic reaction. Keep temperature between 45° C. to 60° C.
3. Add MEA at a controlled rate. Keep temperature between 60° C. to 70° C.
4. Stir vessel for 1 to 2 hours.
5. At 25° C., add glacial acetic acid, methanol, Bellasol S30, and water.
6. Stir for 30 minutes.
7. Product Finished Testing (Quality Control)

Specific gravity: 1.0506, range: 1.04-1.06

Appearance: light yellow, clear, uniform pH: 9.9, range 9-11

The product was designated Composition A and contained the following triazines:

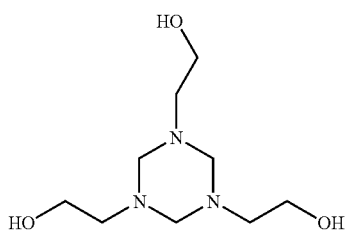
(II)

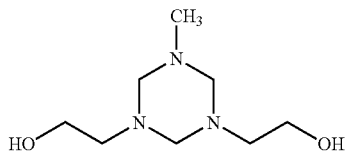
(III)

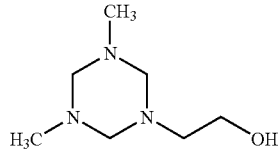
(IV)

(V)

Example 2

Field Trial

The inventive Composition A of Example 1 was compared with HSW700 (a MEA triazine $H_2S$ scavenger made from MEA and formaldehyde available from Baker Petrolite) in a field trial to remove $H_2S$ from natural gas. At the gas plant where the field trial was performed, it was necessary to lower the $H_2S$ in the natural gas to below 4 lbs/hr (1.8 kg/hr). The inventive Example 1 material had a 15% higher capacity for $H_2S$ removal and lower raw material cost as compared with HSW700. Shown in FIG. 1 is a graph of the ratio of $H_2S$ mass uptake to the mass of scavenger as a function of time for the inventive Example 1 triazine (Composition A) compared to the HSW700 monoethanolamine triazine product having no alkylamine functionality. It will be seen that the Example 1 material takes up $H_2S$ faster and with greater capacity in contrast to the HSW700 ability.

The optimum theoretical capacity for HSW700 is 1.17 lbs (0.14 kg/liter) $H_2S$ removed/gal of scavenger with an upper limit of 1.78 lbs (0.21 kg/liter) $H_2S$ removed/gal of scavenger (when the chemical is overspent). The calculated optimum capacity of the inventive Example 1 scavenger is 1.36 (0.16 kg/liter) with an upper limit of 2.04 lbs $H_2S$ removed/gal of scavenger (0.24 kg/liter). During the field trial, the two products were compared under four different scenarios with the following results:

a. Lower than theoretically optimum dosage: Inventive Example 1 scavenger consumption rate is 17% lower than HSW700, where the consumption rate difference is calculated as:

$$\text{Consumption Rate \% Difference} = \left(\frac{\text{Consumption Rate Difference } betw \text{ } HSW700 \text{ and Ex. 1}}{\text{Average of Consumption Rate of } HSW700 \text{ and Ex. 1}}\right) \times 100$$

b. Excess $H_2S$ and long contact time: Inventive Example 1 scavenger consumption rate is 53% lower than HSW700.

c. Optimum dosage: Inventive Example 1 scavenger consumption rate is 30% lower than HSW700.
d. Higher than optimum dosage: No difference in consumption rate.

From the above Examples it may be seen that the inventive Example 1 scavenger is a higher efficiency scavenger than the HSW700 product, and thus achieves the goals of a fast, high capacity scavenger. It will be appreciated that it is not necessary for the sulfhydryl compound scavengers herein to remove all of the sulfhydryl compound from the substrate for the method and compositions herein to be considered successful in accomplishing the desired goals.

In the foregoing specification, the invention has been described with reference to specific embodiments thereof, and has been demonstrated as effective in reducing sulfhydryl compound contents for substrates containing them. However, it will be evident that various modifications and changes can be made thereto without departing from the broader spirit or scope of the invention as set forth in the appended claims. Accordingly, the specification is to be regarded in an illustrative rather than a restrictive sense. For example, specific combinations of reactants to make the triazine scavengers other than those specifically exemplified herein may be used. Further, triazine scavengers and other components, as well as different substrates falling within the claimed parameters, but not specifically identified or tried in a particular composition or method, are anticipated to be within the scope of this invention.

What is claimed is:

1. A method for reducing an amount of sulfhydryl compounds in sour aqueous or sour hydrocarbon substrates, or combinations thereof, comprising scavenging said sulfhydryl compounds from said substrate with a scavenging agent comprising a triazine having both hydroxyalkyl and alkylamine functionality, the agent present in an amount sufficient to reduce said amount of said sulfhydryl compounds in said substrate.

2. The method of claim 1 where the triazine has the structure:

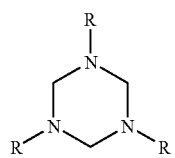

(I)

where the R groups are independently selected from the group consisting of $C_1$-$C_{20}$ straight or branched alkyl groups and —$R_1$OH, where $R_1$ is a $C_1$-$C_{20}$ straight or branched alkylene group, provided that at least one R group is $C_1$-$C_{20}$ straight or branched alkyl groups and at least one R group is —$R_1$OH.

3. The method of claim 2 where at least one R group is —$R_1$OH where $R_1$ is $C_2$ alkylene, and where at least one R group is methyl.

4. The method of claim 1 where the scavenging agent is formed by reacting formaldehyde with at least one primary amine and at least one alkanolamine, such that the molar ratio of formaldehyde to total amines ranges from about 2:1 to about 1:2.

5. The method of claim 4 where the primary amine and the alkanolamine each contain 1 to 20 carbon atoms.

6. The method of claim 5 where the primary amine is selected from the group consisting of methylamine, ethylamine, propylamine, isopropylamine, butylamine, iso-butylamine and mixtures thereof.

7. The method of claim 5 where the alkanolamine is selected from the group consisting of ethanolamine (2-aminoethanol), iso-propanolamine (1-amino -2-propanol), aminopropanol (3-amino-1-propanol), aminomethylpropanol (2-amino-2-methylpropanol), trishydroxymethylmethylamine (2-amino-2-hydroxymethyl-1,3-propanediol) and mixtures thereof.

8. The method of claim 1 where the substrate is gas and the amount of scavenging agent ranges from about 0.00045 to about 13.4 gallons per ppm of sulfhydryl compound×MMscf of gas (about 0.06 to about 1790 liters scavenger used/(ppm sulfhydryl compound removed×MMscm)).

9. The method of claim 1 where the substrate is natural gas and at least one of the sulfhydryl compounds is hydrogen sulfide.

10. A method for reducing an amount of sulfhydryl compounds in sour hydrocarbon gas comprising contacting a sour hydrocarbon gas comprising at least one sulfhydryl compound with a triazine scavenging agent present in an amount ranging from about 0.00045 to about 13.4 gallons per ppm of sulfhydryl compound×MMscf of gas (about 0.06 to about 1790 liters scavenger used/(ppm sulfhydryl compound removed×MMscm)), where the triazine has the structure:

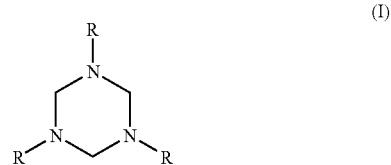

(I)

where the R groups are independently selected from the group consisting of $C_1$-$C_{20}$ straight or branched alkyl groups and —$R_1$OH, where $R_1$ is a $C_1$-$C_{20}$ straight or branched alkylene group, provided that at least one R group is $C_1$-$C_{20}$ straight or branched alkyl groups and at least one R group is —$R_1$OH.

11. The method of claim 10 where at least one R group is —$R_1$OH where $R_1$ is $C_2$ alkylene, and where at least one R group is methyl.

12. The method of claim 10 where the sour hydrocarbon gas is natural gas and at least one of the sulfhydryl compounds is hydrogen sulfide.

13. A substrate treated to reduce the presence of at least one sulfhydryl compound comprising:

a sour substrate selected from the group consisting of sour aqueous substrates, sour hydrocarbon substrates, and mixtures thereof, the substrate containing at least one sulfhydryl compound; and a scavenging agent comprising a triazine having both hydroxyalkyl and alkylamine functionality, the agent present in an amount sufficient to reduce the amount of the at least one sulfhydryl compound in the substrate as compared with the same substrate absent the scavenging agent.

14. The substrate of claim 13 where the triazine has the structure:

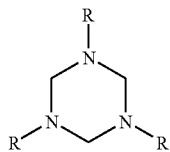

where the R groups are independently selected from the group consisting of $C_1$-$C_{20}$ straight or branched alkyl groups and —$R_1OH$, where $R_1$ is a $C_1$-$C_{20}$ straight or branched alkylene group, provided that at least one R group is $C_1$-$C_{20}$ straight or branched alkyl groups and at least one R group is —$R_1OH$.

15. The substrate of claim 14 where at least one R group is —$R_1OH$ where $R_1$ is $C_2$ alkylene, and where at least one R group is methyl.

16. The substrate of claim 13 where the scavenging agent is formed by reacting formaldehyde with at least one primary amine and at least one alkanolamine, such that the molar ratio of formaldehyde to total amines ranges from about 2:1 to about 1:2.

17. The substrate of claim 16 where the primary amine atoms and the alkanolamine each contain 1 to 20 carbon atoms.

18. The substrate of claim 17 where the primary amine is selected from the group consisting of methylamine, ethylamine, propylamine, isopropylamine, butylamine, iso-butylamine and mixtures thereof.

19. The substrate of claim 17 where the alkanolamine is selected from the group consisting of ethanolamine (2-aminoethanol), iso-propanolamine (1-amino-2-propanol), aminopropanol (3-amino-1-propanol), aminomethylpropanol (2-amino-2-methylpropanol), trishydroxymethylmethylamine (2-amino-2-hydroxymethyl-1,3-propanediol) and mixtures thereof.

20. The substrate of claim 13 where the substrate is gas and the amount of scavenging agent ranges from about 0.00045 to about 13.4 gallons per ppm of sulfhydryl compound×MMscf of gas (about 0.06 to about 1790 liters scavenger used/(ppm sulfhydryl compound removed×MMscm)).

21. The substrate of claim 13 where the substrate is natural gas and at least one of the sulfhydryl compounds is hydrogen sulfide.

22. A sour hydrocarbon gas treated to reduce the presence of at least one sulfhydryl compound comprising:
a sour hydrocarbon gas containing at least one sulfhydryl compound; and
a scavenging agent in an amount of from about 0.00045 to about 13.4 gallons per ppm of sulfhydryl compound× MMscf of gas (about 0.06 to about 1790 liters scavenger used/(ppm sulfhydryl compound removed×MMscm)), a scavenging agent comprising a triazine has the structure:

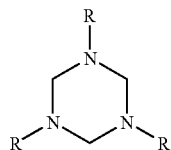

where the R groups are independently selected from the group consisting of $C_1$-$C_{20}$ straight or branched alkyl groups and —$R_1OH$, where $R_1$ is a $C_1$-$C_{20}$ straight or branched alkylene group, provided that at least one R group is $C_1$-$C_{20}$ straight or branched alkyl groups and at least one R group is —$R_1OH$.

23. The sour hydrocarbon gas of claim 22 where in the triazine at least one R group is —$R_1OH$ where $R_1$ is $C_2$ alkylene, and where at least one R group is methyl.

24. The sour hydrocarbon gas of claim 22 where the sour hydrocarbon gas is natural gas and at least one of the sulfhydryl compounds is hydrogen sulfide.

* * * * *